United States Patent [19]
Brennan

[11] Patent Number: 5,970,428
[45] Date of Patent: Oct. 19, 1999

[54] GROUND LOOP DETECTOR CIRCUIT AND METHOD

[75] Inventor: Stephen Michael Brennan, Reno, Nev.

[73] Assignee: Elsag International N.V., Amsterdam, Netherlands

[21] Appl. No.: 08/947,068

[22] Filed: Oct. 8, 1997

[51] Int. Cl.[6] .................................................. G01N 27/00
[52] U.S. Cl. ............................ 702/58; 702/65; 324/425
[58] Field of Search ............................. 702/58, 64, 65; 324/438, 444, 510, 425

[56] References Cited

U.S. PATENT DOCUMENTS

| | | | |
|---|---|---|---|
| 3,661,748 | 5/1972 | Blackmer | 324/425 |
| 3,774,106 | 11/1973 | MacPhee | 324/510 |
| 4,118,663 | 10/1978 | Barben, II | 324/443 |
| 4,777,444 | 10/1988 | Beijk et al. | 324/439 |
| 5,268,852 | 12/1993 | Forsythe et al. | 702/58 |
| 5,630,921 | 5/1997 | Hess et al. | 204/435 |
| 5,666,255 | 9/1997 | Muelleman | 361/111 |

*Primary Examiner*—Marc S. Hoff
*Assistant Examiner*—Bryan Bui
*Attorney, Agent, or Firm*—Michael M. Rickin

[57] ABSTRACT

A ground loop detector circuit and method for an instrument that is used with either a pH sensor or a conductivity sensor. In the instrument used with a pH sensor, an AC diagnostic signal is provided to the sensor. A high input impedance diagnostic signal monitor monitors the voltage at a node adjacent the output of the diagnostic signal source. The occurrence of a ground loop causes the voltage at the node to drop. The instrument used with the conductivity sensor, not only monitors current returning to the diagnostic circuitry from the sensor but also uses a high input impedance monitor to monitor the current leaving the diagnostic circuit to the sensor. The relationship between the current from the sensor and the current to the sensor can be used to determine if a ground loop has occurred as such a loop will cause the current from the sensor to be less than the current to the sensor.

11 Claims, 2 Drawing Sheets

GROUND LOOP DETECTOR CIRCUIT AND METHOD

FIELD OF THE INVENTION

This invention relates to diagnostic circuitry for process instrumentation and more particularly to a diagnostic circuit and method that detects a ground loop.

DESCRIPTION OF THE PRIOR ART

Process variables such as pH and conductivity are measured using sensors unique in design for the chemical property of interest. The sensors are connected to an instrument, such as a transmitter, so that a signal representative of the value of the measured process variable can be provided to an operator or to equipment used to control the process.

As is well known, a ground loop, that is an errant galvanic path caused by unwanted circuit connections provided by the earth or chassis ground, in the sensor or the instrument will cause an offset or instability in the value of the measured process variable. A ground loop may arise as a result of a number of causes. One such cause is a nick in the insulation of one of the cables used in connecting the sensor to the instrument. Another such cause is a leak in the sensor. Yet another such cause are problems with the electronic components used in the instrument. For example, a ground loop may arise as a result of the breakdown of the filter capacitors used in the instrument's power supply.

The amount of offset or instability in the value of the measured process variable caused by a ground loop depends on the impedance of the ground loop. When the ground loop impedance is very high, the offset or instability will be very small and may not even be noticed. When the ground loop impedance is low the offset will be larger. The impedance of a ground loop may decrease with time thereby causing an increase with time of the offset or instability in the value of the measured process variable.

As can be appreciated from the preceding description it is desirable for the instrument measuring the process variable to automatically detect the occurrence of a ground loop. Such detection will allow the equipment controlling the process and the individuals responsible for operating and maintaining the process to be notified that a ground loop has occurred.

While diagnostic circuitry has been included in instruments used to measure pH, see for example U.S. Pat. Nos. 3,661,748; 4,777,444; and 5,268,852, none of those diagnostic circuits detect the occurrence of a ground loop. The traditional method used in pH measurement for detecting if a drift in the pH measurement is due to a ground loop is to measure the reading of the suspected sensor against a known reference.

Instruments used in the measurement of conductivity may include diagnostic circuitry to alert the user that the sensor is fouled or a that there is a break in one of the cables connecting the sensor to the instrument. Such diagnostic circuitry does not, however, detect the occurrence of a ground loop. The traditional method used to determine if the reading of an in process conductivity sensor is correct is to measure the conductivity of the process solution using a known good out of process sensor. While this method will show that the in process conductivity sensor is giving an incorrect reading, it does not provide any indication of the source of the incorrect reading. The incorrect reading may be the result of a ground loop or a problem with the sensor or instrument.

Therefore, in instruments used to measure pH and conductivity it is desirable to have diagnostic circuitry and a method that detects the occurrence of a ground loop.

SUMMARY OF THE INVENTION

The present invention is embodied as a circuit for detecting the occurrence of a ground loop in instrumentation used to measure a variable of a process. The circuit has a source for providing an AC diagnostic signal with a known frequency to a sensor. The sensor is in electrical contact with the process for measuring the process variable and providing a DC signal having a level representative of the process variable.

The circuit also has a high input impedance monitor connected to a node that is located between the source and the sensor. The circuit further has a predetermined impedance at the known frequency connected between the source and the node. The circuit further also has a low impedance input circuit that acts as a virtual ground to the DC signal level and the AC diagnostic signal. The low impedance input circuit is connected to the sensor to thereby provide a return path from the sensor to the source. The occurrence of a ground loop causes the voltage at the node to decrease by an amount that is inversely related to the impedance of the ground loop.

The present invention is also embodied as a circuit for detecting the occurrence of a ground loop. The circuit is in an instrument which is used in combination with a sensor that is in electrical contact with a process to measure a variable of the process and provide a DC signal having a level representative thereof. The circuit has a source, a high input impedance monitor, a predetermined impedance, and a low impedance input circuit all of which are connected and function in the manner described above for the like named elements.

The present invention is further embodied as a circuit for detecting the occurrence of a ground loop. The circuit is in an instrument which is used in combination with a sensor that is in electrical contact with a process to measure a variable of the process. The circuit has a source for providing an AC diagnostic signal current with a known frequency to the sensor.

The circuit also has means connected to the source for measuring the provided AC diagnostic signal current. The circuit further has a predetermined impedance at the known frequency connected between the source and the provided current measuring means. The circuit also further has means for measuring the amount of the provided AC diagnostic signal current which returns to the source from the sensor. The occurrence of a ground loop causes the voltage at the means for measuring the amount of the provided AC diagnostic signal current which returns to the source from the sensor to decrease by an amount that is inversely related to the impedance of the ground loop.

The present invention is also embodied as a method for detecting the occurrence of a ground loop. The method is performed in an instrument which is used in combination with a sensor that is in electrical contact with a process to measure a variable of the process and provide a DC signal having a level representative thereof. The method has the step of providing an AC diagnostic signal with a known frequency to the sensor.

The method also has the step of measuring by a high input impedance monitor the voltage at a node that is located between the source and the sensor, a predetermined impedance at the known frequency connected between the source and the node. The method also has the further step of providing a return path from the sensor to the source by a low impedance input circuit that acts as a virtual ground to the DC signal level and the AC diagnostic signal thereon. The occurrence of a ground loop causes the voltage at the node to decrease by an amount that is inversely related to the impedance of the ground loop.

The present invention is also embodied as a method for detecting the occurrence of a ground loop. The method is performed in an instrument which is used in combination with a sensor that is in electrical contact with a process to measure a variable of the process. The method has the step of providing an AC diagnostic signal current with a known frequency to the sensor.

The method also has the step of measuring the provided AC diagnostic signal current. The method further has the step of connecting a predetermined impedance at the known frequency between the source and the provided current measuring means. The method further has the step of measuring the amount of the provided AC diagnostic signal current which returns to the source from the sensor. The occurrence of a ground loop causes the voltage at the means for measuring the amount of the provided AC diagnostic signal current which returns to the source from the sensor to decrease by an amount that is inversely related to the impedance of the ground loop.

The invention is also embodied as the combination of:

a) a sensor that is in electrical contact with a process to measure a variable of the process and provide a DC signal having a level representative thereof; and b) an instrument including a circuit for detecting the occurrence of a ground loop, the ground loop occurrence detecting circuit comprising:

i) a source for providing an AC diagnostic signal with a known frequency to the sensor;

ii) a high input impedance monitor connected to a node between the source and the sensor;

iii) a predetermined impedance at the known frequency connected between the source and the node; and iv) a low impedance input circuit that acts as a virtual ground to the DC signal level and the AC diagnostic signal, the low impedance input circuit connected to the sensor to thereby provide a return path from the sensor to the source;

whereby the occurrence of a ground loop causes the voltage at the node to decrease by an amount that is inversely related to the impedance of the ground loop.

The invention is further embodied as the combination of:

a) a sensor that is in electrical contact with a process to measure a variable of the process; and b) an instrument including a circuit for detecting the occurrence of a ground loop, the ground loop occurrence detecting circuit comprising:

i) a source for providing an AC diagnostic signal current with a known frequency to the sensor;

ii) means connected to the source for measuring the provided AC diagnostic signal current;

iii) a predetermined impedance at the known frequency connected between the source and the provided current measuring means; and iv) means for measuring the amount of the provided AC diagnostic signal current which returns to the source from the sensor;

whereby the occurrence of a ground loop causes the voltage at the means for measuring the amount of the provided AC diagnostic signal current which returns to the source from the sensor to decrease by an amount that is inversely related to the impedance of the ground loop.

DESCRIPTION OF THE PREFERRED EMBODIMENT (S)

Figure 1:
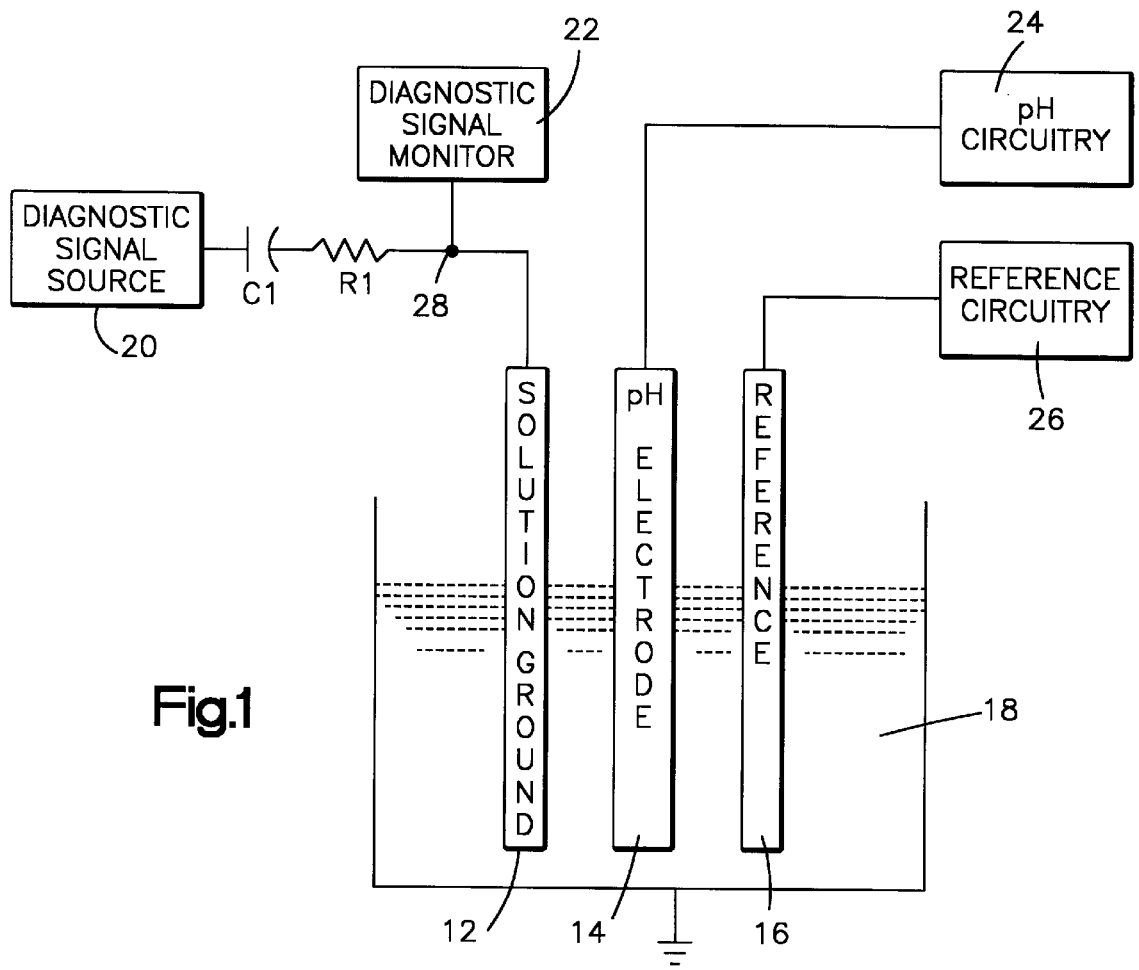
FIG. 1 shows a simplified block and schematic diagram of a process instrument that includes the ground loop detector circuit of the present invention and a sensor for measuring pH of a solution.

Referring now to FIG. 1, there is shown a simplified block and schematic diagram of a process instrument 10 for measuring the pH of a solution. The instrument 10 includes the ground loop detector circuit of the present invention. FIG. 1 also shows in simplified form the solution ground electrode 12, the pH electrode 14 and the reference electrode 16 of the electrochemical sensor which is immersed in a process solution 18 to thereby measure the pH of the solution. One example of such a sensor is shown in U.S. Pat. No. 5,630,921 ("the '921 Patent") which issued on May 20, 1997 and is assigned to the same assignee as is the present invention.

Instrument 10 includes a low impedance diagnostic signal source 20 which provides, through solution ground 12, an AC diagnostic signal to the process solution 18. The signal source 20 is AC coupled through a capacitor C1 and a resistor R1 to solution ground 12. The capacitor C1 prevents the DC current representative of the pH of the process solution from entering the source. In one embodiment of the present invention the AC diagnostic signal was a square wave and had a frequency of 100 Hz and an amplitude of +/−1.2V.

Instrument 10 also includes a diagnostic signal monitor 22 which monitors the voltage of the diagnostic signal at node 28. Monitor 22 is not AC coupled to the sensor but has a high input impedance which keeps all but an extremely small amount of the DC current representative of the pH of the process solution from entering the monitor. As will be described in more detail hereinafter, a ground loop will cause the amplitude of the monitored voltage at node 28 to be lower than it is if there was not a ground loop. The voltage monitored by monitor 22 is signal processed by circuitry (not shown) and sent to a microprocessor (not shown) which can be used to determine if a ground loop has occurred and if so, to provide an appropriate indication of such occurrence. Of course, the voltage monitored by monitor 22 can be displayed to allow the user to decide if a ground loop has occurred.

Instrument 10 also includes the circuitry 24, 26 associated with the pH and reference electrodes 14, 16. The pH circuitry 24 has a high input impedance and provides a DC signal having a level representative of the pH of the process solution and the AC diagnostic signal which is used to provide diagnostics for the pH electrode 14. The reference circuitry 26 has a low input impedance and provides the AC diagnostic signal which is used to provide diagnostics for the reference electrode 16.

As was described above, the source 20 provides the diagnostic signal current to the solution ground electrode. The diagnostic signal current could then flow through the solution 18 and the pH electrode 14 to the pH circuitry 24. The high input impedance of circuitry 24 prevents all but an extremely small amount of the diagnostic signal current from entering using that path. Since the input impedance of the reference circuitry 26 is relatively low, almost all of the diagnostic signal current flows through the solution 18 and the reference electrode 16 to the circuitry 26.

In addition to the current flow paths described above, there are three capacitive paths available to the diagnostic signal current. A first such path is through the filter capacitors located in the power supply (not shown) of instrument 10. The capacitance of those capacitors is such that those capacitors present a very high impedance, as compared to the input impedance of the reference circuitry 26, at the 100 Hz frequency of the diagnostic signal. A second such path is the capacitance of the sensor cable. Typically the cable capacitance is 20 to 30 pF/ft. and the maximum cable length is 100 ft. Thus the additional current draw through this path will only be $\frac{1}{100}^{th}$ of a ground loop current if the circuit of the present invention is used to detect ground loops that are 10 Kohms or less. A third such path is the interwinding capacitance of the isolation transformer in the power supply. Typically this capacitance is in the order of tens of pico farads which translates to hundreds of megohms at the 100 Hz frequency of the diagnostic signal.

Figure 2:
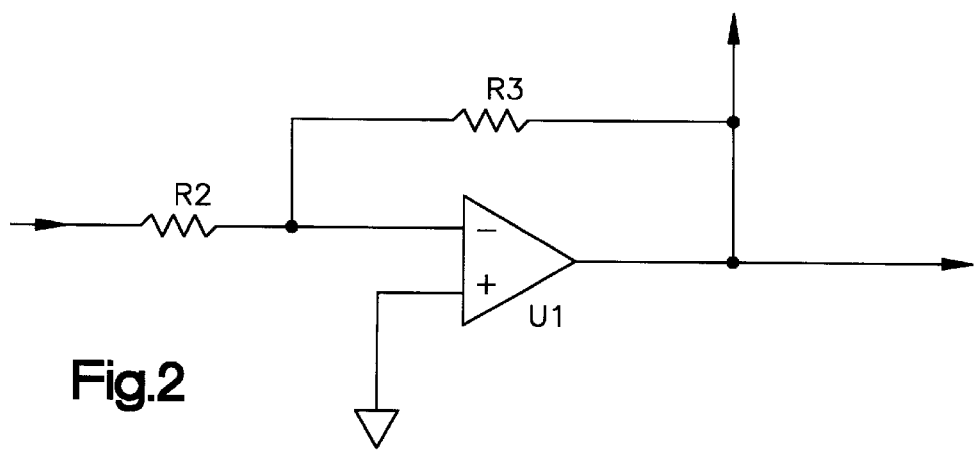
FIG. 2 shows a schematic circuit diagram for one embodiment of a portion of the reference circuitry of FIG. 1.

Referring now to FIG. 2, there is shown a diagram for a portion of one embodiment of the reference circuitry 26. The reference circuitry receives at its input both the AC diagnostic signal and the DC signal having a level representative of the pH of the process solution. These signals are connected through a resistor R2 to the inverting input of an operational amplifier U1. The non-inverting input of amplifier U1 is connected to ground and the output of the amplifier is connected back to the inverting input by a resistor R3. These connections ensure that the inverting input of the amplifier is a virtual ground for both the DC signal level and the AC diagnostic signal riding thereon.

As was described in connection with FIG. 1, the AC diagnostic signal essentially flows only through the reference electrode 16 and the reference circuitry 26. Therefore, the minimum impedance to analog common for the AC diagnostic signal is the sum of the impedance of resistor R2 and the internal impedance of the sensor. Thus, during normal operation without any ground loops the majority of current draw on the diagnostic signal source 12 is the current which flows through the minimum impedance to analog common.

Measurements of a sensor embodied in accordance with the teachings of the '921 Patent have shown that the internal impedance of the reference electrode of such a sensor when new is in the order of 1000 to 2000 ohms. This internal impedance may reach several hundred thousand ohms as the reference electrode ages. In one embodiment for reference circuitry 26, the resistance of R2 was selected to be 100 Kohms. Therefore, in that embodiment the minimum impedance to analog common for the diagnostic signal when the sensor was new is 101 Kohms.

Referring once again to FIG. 1, the diagnostic current, as was previously described, flows through capacitor C1 and resistor R1 to the solution ground electrode 12. Monitor 22 measures diagnostic current flow by measuring the voltage present at the node 28 between resistor R1 and the input to monitor 22. The monitored voltage level at node 28 is pulled down by the voltage divider formed by the impedance of capacitor C1 and resistor R1 and the impedance of the ground loop fault. In one embodiment for instrument 10, the capacitance of capacitor C1 and the resistance of resistor R1 were selected so that the impedance of those elements at the 100 Hz frequency of the diagnostic signal is 3.3 Kohms.

In the one embodiment of instrument 12 described herein the voltage, Vn, at node 28 in the absence of a ground loop is:

Vn=(1.2V)*(101 Kohms)/(3.3 Kohms+101 Kohms)=1.16 volts.

When a ground loop occurs, the impedance of the ground loop is added in parallel to the minimum impedance to analog common for the diagnostic signal. If for example the impedance of the ground loop is 5 Kohms, the parallel combination of the 5 Kohms and the 101 Kohms minimum impedance to analog common for the diagnostic signal becomes 4.764 Kohms. Therefore in the one embodiment of the instrument described herein, the voltage at node 28 drops to 0.71 volts.

Figure 3:
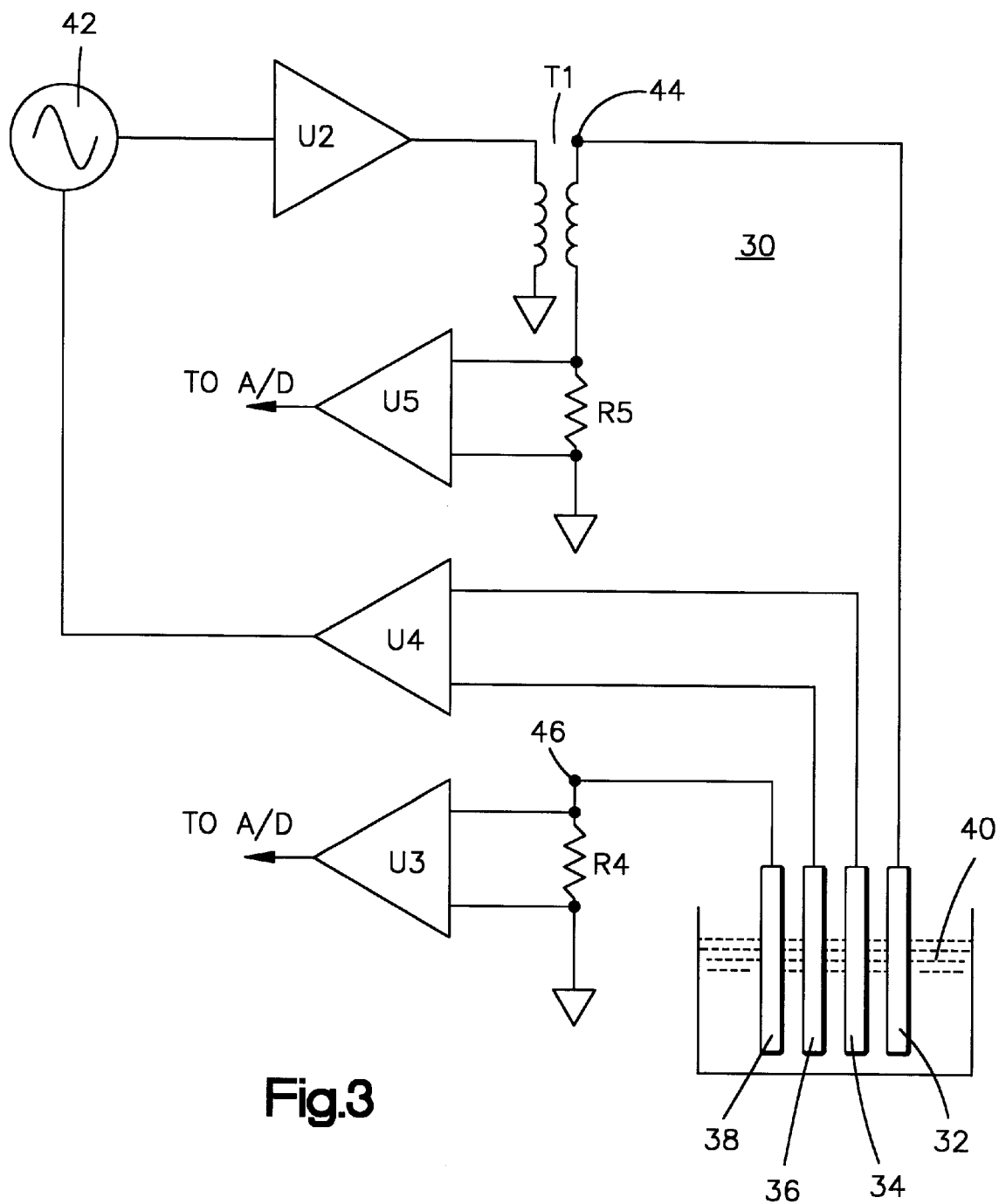
FIG. 3 shows a simplified schematic diagram of a process instrument that includes the ground loop detector circuit of the present invention and a sensor for measuring conductivity of a solution.

Referring now to FIG. 3, there is shown a simplified schematic diagram of a process instrument 30 for measuring the conductivity of a solution. The instrument 30 includes the ground loop detector of the present invention. FIG. 3 also shows in simplified form four electrodes 32, 34, 36 and 38 of a conductivity sensor immersed in solution 40. One example of a four electrode conductivity sensor is shown in U.S. Pat. No. 4,118,663.

The instrument 30 includes an amplitude controlled oscillator 42 which provides an AC signal to the current electrode 32 through amplifier U2 and transformer T1. The AC current flows through the solution 40 to a current electrode 38 which is connected to the inputs of an operational amplifier U3. A resistor R4 is connected across the inputs of U3. The output of amplifier U3 may be connected to a conductivity display (not shown) or to equipment (not shown), such as a microprocessor, for controlling the process.

Instrument 30 also includes a high input impedance amplifier U4 which has its inputs connected to potential sensing electrodes 34 and 36. The electrodes 34 and 36 measure the voltage created in solution 40 by the current electrodes 32 and 38. The output of amplifier U4 is connected to oscillator 42 and is used to control the amplitude of the AC signal at the output of the oscillator to maintain a constant excitation field in the solution 40.

The current returning to the instrument 30 from the solution 40 produces a voltage drop in resistor R4 which is sensed by amplifier U3. The amount of excitation current from oscillator 42 required to maintain a constant excitation field in the solution is directly proportional to solution conductivity. Therefore, the current electrodes 32 and 38 provide the path for the AC current which is used in the determination of the conductivity of the solution 40. As is described in more detail below, the electrodes 32 and 38 also provide the path for the AC current that is used by the circuit of the present invention to detect if a ground loop has occurred.

Instrument 30 also includes an operational amplifier U5 whose input is connected to the secondary winding of transformer T1. A resistor R5, which is used in sensing the amount of current leaving the instrument, is connected across the inputs of amplifier U5. Amplifier U5 has a high input impedance and functions in a manner identical to monitor 22 of FIG. 1. The current leaving the instrument produces a voltage drop across resistor R5 which is sensed by amplifier U5.

In the absence of a ground loop, the current returning to the instrument, which is sensed by resistor R4, should be equal to the current leaving the instrument. Therefore, in the absence of a ground loop there is a known relationship between the voltage drop produced across resistor R5 by the current leaving the instrument and the voltage drop produced across resistor R4 by the current returning to the instrument.

The occurrence of a ground loop will cause the current returning to the instrument to be less than the current leaving the instrument. This disparity in current will change the relationship between the voltages produced across resistors R4 and R5. Equipment (not shown), such as a microprocessor, connected to the outputs of amplifiers U3 and U5 can monitor the relationship between the two voltages and provide an indication of the occurrence of a ground loop when that relationship has changed by a predetermined amount from the relationship that exists in the absence of a ground loop.

In one embodiment of instrument 30, the resistance of resistors R4 and R5 were each selected to be 100 ohms. Therefore assuming that both resistors are ideal, the voltage drop across the resistors will be equal in the absence of a ground loop.

While a four electrode conductivity sensor is shown in FIG. 3, the ground loop detector circuit of the present invention can also be used with a two electrode conductivity sensor. In that instance, the high input impedance amplifier U4 would be connected to nodes 44 and 46 as the potential sensing electrodes 34 and 36 do not exist in a two electrode conductivity sensor. If the ground loop detection circuit of the two electrode conductivity sensor uses synchronous demodulation it may be necessary to include in that circuit compensation for phase shift. As is known by those skilled in the art synchronous demodulation helps eliminate noise and there is not any need to compensate for phase shift if the circuit uses non-synchronous demodulation.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A circuit for detecting the occurrence of a ground loop in instrumentation used to measure a variable of a process comprising:
   a) a source for providing an AC diagnostic signal with a known frequency to a sensor, said sensor in electrical contact with said process for measuring said process variable and providing a DC signal having a level representative of said process variable;
   b) a high input impedance monitor connected to a node between said source and said sensor;
   c) a predetermined impedance at said known frequency connected between said source and said node; and
   d) a low impedance input circuit that acts as a virtual ground to said DC signal level and said AC diagnostic signal, said low impedance input circuit connected to said sensor to thereby provide a return path from said sensor to said source;
   whereby the occurrence of a ground loop causes the voltage at said node to decrease by an amount that is inversely related to the impedance of said ground loop.

2. The circuit of claim 1 wherein said AC diagnostic signal is a square wave.

3. The circuit of claim 1 wherein said AC diagnostic signal known frequency is 100 Hz.

4. The circuit of claim 1 wherein said predetermined impedance connected between said source and said node comprises the combination of a capacitor and a resistor connected in series between said source and said node.

5. In an instrument which is used in combination with a sensor in electrical contact with a process for measuring a variable of said process and providing a DC signal having a level representative of said process variable, a method for detecting the occurrence of a ground loop comprising the steps of:
   a) providing an AC diagnostic signal with a known frequency to said sensor;
   b) measuring by a high input impedance monitor the voltage at a node that is between said source and said sensor, a predetermined impedance at said known frequency connected between said source and said node; and
   c) providing a return path from said sensor to said source by a low impedance input circuit that acts as a virtual ground to said DC signal level and said AC diagnostic signal thereon;
   whereby the occurrence of a ground loop causes the voltage at said node to decrease by an amount that is inversely related to the impedance of said ground loop.

6. In an instrument which is used in combination with a sensor that is in electrical contact with a process to measure a variable of said process, a method for detecting the occurrence of a ground loop comprising the steps of:
   a) providing an AC diagnostic signal current with a known frequency to said sensor;
   b) measuring said provided AC diagnostic signal current;
   c) connecting a predetermined impedance at said known frequency between said source and said provided current measuring means; and
   d) measuring the amount of said provided AC diagnostic signal current which returns to said source from said sensor;
   whereby the occurrence of a ground loop causes the voltage at said means for measuring the amount of said provided AC diagnostic signal current which returns to said source from said sensor to decrease by an amount that is inversely related to the impedance of said ground loop.

7. In combination:
   a) a sensor that is in electrical contact with a process to measure a variable of said process and provide a DC signal having a level representative thereof; and
   b) an instrument including a circuit for detecting the occurrence of a ground loop, said ground loop occurrence detecting circuit comprising:
      i) a source for providing an AC diagnostic signal with a known frequency to said sensor;
      ii) a high input impedance monitor connected to a node between said source and said sensor;
      iii) a predetermined impedance at said known frequency connected between said source and said node; and
      iv) a low impedance input circuit that acts as a virtual ground to said DC signal level and said AC diagnostic signal, said low impedance input circuit connected to said sensor to thereby provide a return path from said sensor to said source;
   whereby the occurrence of a ground loop causes the voltage at said node to decrease by an amount that is inversely related to the impedance of said ground loop.

8. The combination of claim 7 wherein said AC diagnostic signal is a square wave.

9. The combination of claim 7 wherein said AC diagnostic signal known frequency is 100 Hz.

10. The combination of claim 7 wherein said predetermined impedance in said ground loop detecting circuit is connected between said source and said node comprises the combination of a capacitor and a resistor connected in series between said source and said node.

11. In combination:
   a) a sensor that is in electrical contact with a process to measure a variable of said process; and
   b) an instrument including a circuit for detecting the occurrence of a ground loop, said ground loop occurrence detecting circuit comprising:
      i) a source for providing an AC diagnostic signal current with a known frequency to said sensor;
      ii) means connected to said source for measuring said provided AC diagnostic signal current;
      iii) a predetermined impedance at said known frequency connected between said source and said provided current measuring means; and
      iv) means for measuring the amount of said provided AC diagnostic signal current which returns to said source from said sensor;
   whereby the occurrence of a ground loop causes the voltage at said means for measuring the amount of said provided AC diagnostic signal current which returns to said source from said sensor to decrease by an amount that is inversely related to the impedance of said ground loop.

* * * * *